(12) United States Patent
Lowenstein et al.

(10) Patent No.: US 6,635,237 B2
(45) Date of Patent: Oct. 21, 2003

(54) PHARMACEUTICAL COMPOSITION BASED ON COCAETHYLENE AND USE THEREOF FOR TREATING PSYCHOACTIVE SUBSTANCE DEPENDENCE

(75) Inventors: William Lowenstein, Paris (FR); Mario Sanchez, Paris (FR); Benedicte Lepere-Prevot, Paris (FR); Benjamin De Rothschild, Chambesy (CH)

(73) Assignee: Debussy Holding SA (LU)

( * ) Notice: Subject to any disclaimer, the term of this patent is extended or adjusted under 35 U.S.C. 154(b) by 0 days.

(21) Appl. No.: 10/049,061

(22) PCT Filed: May 18, 2001

(86) PCT No.: PCT/FR01/01544
§ 371 (c)(1),
(2), (4) Date: Jun. 10, 2002

(87) PCT Pub. No.: WO02/05817
PCT Pub. Date: Jan. 24, 2002

(65) Prior Publication Data
US 2002/0188002 A1 Dec. 12, 2002

(30) Foreign Application Priority Data
Jul. 18, 2000 (FR) .............................. 00/09408

(51) Int. Cl.$^7$ .................... A61K 9/64; A61K 31/44
(52) U.S. Cl. .................... 424/48; 424/468; 514/304
(58) Field of Search .................... 514/304; 424/48, 424/408

(56) References Cited

U.S. PATENT DOCUMENTS

| | | | | |
|---|---|---|---|---|
| 4,512,996 | A | | 4/1985 | Somers |
| 5,760,044 | A | * | 6/1998 | Archer ................ 514/282 |
| 6,114,508 | A | * | 9/2000 | Scherrmann et al. ....... 435/188 |
| 6,210,677 | B1 | * | 4/2001 | Bohannon ................ 424/193.1 |
| 2002/0064529 | A1 | * | 11/2001 | Bohannon ................ 424/184.1 |

FOREIGN PATENT DOCUMENTS

WO WO 97/42950 11/1997
WO WO 98/42359 10/1998

OTHER PUBLICATIONS

Bradberry Charles W et al: "Rapid induction of behavioral and neurochemical tolerance to cocaethylene, a model compound for agonist therapy of cocaine dependence.", Psychopharmacology, vol. 146, No. 1, 1999, pp. 87–92, XP000992247. ISSN: 0033–3158.
Carroll, F. Ivy et al: "Cocaine and 3. beta–(4'–Substituted phenyl)tropane–2.beta.–carboxylic Acid Ester and Amide Analogs. New High–Affinity and Selective Compounds for the Dopamine Transporter", J. Med. Chem. (1995), 38(2), 379–88, XP000990413.
Schuelke, Guy S. et al: "Cocaine analgesia: an in vivo structure–activity study", Pharmacol. Biochem. Behav. (1996), 53(1), 133–40, XP000992135.
McCance E.F. et al: "Cocaethylene: Pharmacology, physiology and behavioral effects in humans.", Journal of Pharmacology and Experimental Therapeutics, (1995) 274/1 (215–223)., XP000992238.
Elsworth John D et al: "Serotonin involvement in cocaine sensitization: Clues from studies with cocaine analogs.", Drug Development Research, vol. 30, No. 3, 1993, pp. 189–200,XP000992240, ISSN: 0272–4391.
Raven M.A. et al: "Comparison of the reinforcing and anxiogenic effects of intravenous cocaine and cocaethylene.", Experimental and Clinical Psychopharmacology, (2000) 8/1 (117–124)., XP000992251.
Horowitz, Judith M. et al: "Cocaethylene: effects on brain systems and behavior", Addict. Biol. (1999), 4(2), 127–140, XP000992235.
Hart et al, Psychopharmacology (2000) 149:153–162.
Perez–Reyes et al, Psychopharmacology (1994) 116:428–432.

* cited by examiner

Primary Examiner—James H Reamer
(74) Attorney, Agent, or Firm—Nixon & Vanderhye, P.C.

(57) ABSTRACT

The present invention relates to a pharmaceutical composition comprising cocaethylene as active ingredient and to its use in treating dependence on psychoactive substances, in particular on cocaine.

14 Claims, No Drawings

PHARMACEUTICAL COMPOSITION BASED ON COCAETHYLENE AND USE THEREOF FOR TREATING PSYCHOACTIVE SUBSTANCE DEPENDENCE

The application is the US national phase of international application PCT/FR01/01544 filed May 18, 2001, which designated the U.S.

The present invention relates to a pharmaceutical composition comprising cocaethylene as active ingredient and to its use in the treatment of dependence on psychoactive substances.

There are many psychoactive substances, such as alcohol, amphetamines, cocaine, ecstasy, opiate derivatives, such as opium or heroin, LSD, tobacco or cannabis, which, in addition to their harmful effects on the body, lead to high dependence of the users of these substances.

These substances induce modifications at several levels in the central nervous system and in particular at the level of the combined dopaminergic, serotoninergic and noradrenergic systems. It is recognized that the imbalances, both increase and reduction, in these systems are furthermore the cause of pathological changes, such as schizophrenia or depressive or manic-depressive processes and are probably involved in producing hallucinatory phenomena. Abuse of the abovementioned psychoactive substances is involved and produces "fertile" or "productive" moments in the abovementioned pathologies.

Apart from taking care of opiate-dependent patients by "maintenance" treatments with methadone and buprenorphine, there is currently no specific agonist treatment in the field of addiction. Numerous therapeutic trails have been followed, such as the agonist-antagonist action for the dopaminergic receptors or the action on the serotoninergic system.

Furthermore, for taking care of cocaine-dependent patients, the use of anticocaine antibodies or of anticocaine vaccine has been envisaged. However, there is no specific agonist treatment for treating dependence on cocaine.

It therefore seems important to demonstrate an active compound which makes it possible to act as agonist with respect to the action of cocaine, that is to say which acts on the same structures and in the same sense, and to prepare pharmaceutical compositions comprising this compound as active agent for treating dependence on psychoactive substances.

Cocaethylene binds to the dopamine transporter, thus blocks reuptake of dopamine and therefore leads to a rise in the level of dopamine in the structures of the central nervous system and in particular the dopaminergic system, including the nucleus accumbens.

International Patent Application WO 99/56747 discloses pharmaceutical compositions used for the treatment of dependence on heroin, narcotics, cocaine, amphetamines and marijuana comprising, as active ingredients, two neuroleptic components used simultaneously, AMPT (alpha-methyl-para-tyrosine) and haloperidol, which is a compound of the butyrophenone series. Haloperidol acts as antagonist for the post-synaptic dopaminergic receptors and AMPT acts as negative regulator of the dopamine receptor.

Patent Application WO 97/42950 discloses a method for the treatment of dependence on cocaine and amphetamines by the use of a compound derived from benzomorphan.

The Applicants have discovered, surprisingly, that cocaethylene or ethyl ester of benzoylecgonine can be used as active substance in a pharmaceutical composition, in particular for treating dependence on psychoactive substances.

The present invention relates to the administration to man, in an acceptable pharmaceutical dosage form, of cocaethylene or ethyl ester of benzoylecgonine as therapeutic agent. A subject-matter of the present invention is thus a pharmaceutical composition and a medicament comprising, as active agent, the ethyl ester of benzoylecgonine and their uses in treating dependence on psychoactive substances.

The main subject-matter of the present invention is a pharmaceutical composition comprising, as active ingredient, the ethyl ester of benzoylecgonine, in the form of the free base or of its pharmaceutically acceptable salts, in a pharmaceutically acceptable medium.

The pharmaceutical composition can comprise from 0.1 to 50% and preferably from 0.5 to 10% by weight of ethyl ester of benzoylecgonine with respect to the total weight of the composition.

The ethyl ester of benzoylecgonine can be in the form of the free base or of its pharmaceutically acceptable salts generally used in pharmacology.

The pharmaceutically acceptable salts are chosen, for example, from the salts of inorganic or organic acids, such as the hydrochloride, hydrobromide, nitrate, sulphate, phosphate, formate, acetate, trifluoroacetate, fumarate, oxalate, tartrate, maleate, citrate, succinate, malate, methanesulphonate, benzenesulphonate and p-toluenesulphonate, from the salts of amino acids, such as arginine, lysine, ornithine, aspartic acid and glutamic acid, or from the carboxylate or sulphonate cation resins.

The cation resin is an ion-exchange resin capable of binding positively charged ions (cations). Use may be made, in addition to the cation resin, of any other compound which makes possible slow release of the cocaethylene in the body of the patient.

The ethyl ester of benzoylecgonine can thus be found, for example, in the form of a carboxylate cation resin.

The pharmaceutical composition can additionally comprise pharmaceutically acceptable excipients, such as lactose, sucrose, D-mannitol, crystalline cellulose, starch or any other type of excipient generally used in pharmacology, and pharmaceutically acceptable adjuvants, such as wetting agents, isotonicity agents, emulsifiers, dispersants, stabilizers, solvents, binders, flavouring agents, plasticizers, antioxidants, mastication substances, colorants, preservatives, buffers, sweeteners or any other type of adjuvant generally used in pharmacology.

The amounts of these various adjuvants are those conventionally used in the field under consideration.

Of course, a person skilled in the art will take care to choose the optional compound or compounds to be added to the composition according to the invention so that the advantageous properties intrinsically attached to the composition in accordance with the invention are not, or not substantially, detrimentally affected by the envisaged addition.

The pharmaceutical composition may be intended for oral, percutaneous, buccal or nasal administration or for administration by any other acceptable administration route. When the composition is intended for oral administration, it is provided in the form of a solution, gelatin capsules, tablets, syrup or suspension.

When it is intended for percutaneous administration, it is provided in the form of a transdermal device, such as a patch, or gel.

When it is intended for administration by the buccal route, it is provided in the form of a chewing gum or sublingual tablets.

When it is intended for nasal administration, it is provided in the form of a spray.

Another subject-matter of the present invention is a medicament for treating dependence on psychoactive substances comprising, as active ingredient, the ethyl ester of benzoylecgonine, in the form of the free base or of its pharmaceutically acceptable salts, in a pharmaceutically acceptable medium.

The medicament can be used to treat dependence on psychoactive substances and in particular cocaine, alcohol, amphetamines, ecstasy, heroin, morphine, LSD, cannabis, tobacco and narcotics.

The daily dose of medicament to be administered varies according to the degree of dependence, the method of administration and the weight of the patient. The unit dose of this form administered to man is between 2 and 1,000 milligrams and preferably between 5 and 500 milligrams per unit taken. It may have to be taken between 1 and 20 times daily.

According to a preferred form of the invention, the medicament can be used to treat dependence on cocaine.

The medicament can also be used to treat conditions concomitant with the use of psychoactive substances in the context of fertile or productive moments of pathologies such as schizophrenia, manic-depressive psychosis, paranoia or hallucinatory phenomena. It can, furthermore, be combined with dopamine receptor inhibitors and/or with selective serotonin reuptake inhibitors, in combination with opiate derivatives used in therapy or any other thymic regulatory treatment.

Another subject-matter of the present invention is the use of cocaethylene in the preparation of a medicament for treating dependence on psychoactive substances and more particularly for treating dependence on cocaine, alcohol, amphetamines, ecstasy, heroin, morphine, LSD, cannabis, tobacco or narcotics and more preferably still for treating dependence on cocaine.

Cocaethylene can also be used in the preparation of a medicament for treating mental conditions concomitant with the use of psychoactive substances in the context of schizophrenia, manic-depressive psychosis, paranoia and other psychoses with a hallucinatory form.

The examples which follow are intended to illustrate the invention.

EXAMPLE OF FORMULATIONS COMPRISING COCAETHYLENE

Example 1

Medicinal Chewing Gum

| | |
|---|---|
| Cocaethylene (A.P.) in the form of a carboxylate cation resin | 10 mg A.P. |
| Sodium bicarbonate | 10 mg |
| Anhydrous sodium carbonate | 20 mg |
| Dreyco ® gum | 750 mg |
| Sorbitol | 160 mg |
| 70% Crystallizable sorbitol | 40 mg |
| 85% Glycerol | 10 mg |
| Flavouring agents, sufficient amount | |

The Dreyco® gum is composed of:
synthetic mastication substances: copolymer of isobutylene and of isopropene, petroleum-derived wax, poly(vinyl acetate), polyethylene, polyisobutylene.
plasticizers: glyceryl esters of rosin, glyceryl esters of polymerized rosin, hydrogenated vegetable oils, glyceryl monostearate.
water-insoluble substances: calcium carbonate.
antioxidants: butylated hydroxytoluene.

Example 2

Transdermal device ("patch")

The cocaethylene is present in an amount sufficient for a release which can range from 50 mg to 100 mg for a cutaneous application of 24 hours.

The outer covering is composed of polyester film, the adhesive layer is composed of polyisobutylene with a moderate molecular mass, of polyisobutylene with a low molecular mass and of polybutylene, the nonwoven backing is composed of nonwoven polyester film and the detachable protective sheet is composed of silicone-treated polyester film.

What is claimed is:

1. Pharmaceutical composition comprising, as active ingredient, the ethyl ester of benzoylecgonine, in the form of the free base of its pharmaceutically acceptable salts, in the form of a chewing gum or sublingual tablets.

2. Composition according to claim 1, wherein said ethyl ester of benzoylecgonine is present in an amount of from 0.1 to 50% by weight with respect to the total weight of the composition.

3. Composition according to claim 1, wherein said ethyl ester of benzoylecgonine is present in an amount of from 0.5 to 10% by weight with respect to the total weight of the composition.

4. Composition according to claim 1, wherein the pharmaceutically acceptable salt is a salt of an inorganic acid or an organic acid.

5. Composition according to claim 1 wherein the ethyl ester of benzoylecgonine is in the form of a carboxylate cation resin.

6. Composition according to claim 1, which further comprises at least one pharmaceutically acceptable excipient or adjuvant.

7. A method of treating dependence on psychoactive substances comprising administering to a person dependent on a psychoactive substance a composition comprising, as active ingredient, the ethyl ester of benzoylecgonine, in the form of the free base or of its pharmacceutically acceptable salts, in the form of a chewing-gum or sublingual tablets.

8. A method according to claim 7, wherein said psychoactive substance is selected from the group consisting of cocaine, alcohol, amphetamines, ecstasy, heroin, morphine, LSD, cannabis, tobacco and narcotics.

9. A method according to claim 7, wherein said psychoactive substance is cocaine.

10. A method of treating mental conditions concomitant with the use of psychoactive substances in the context of psychological pathologies comprising administering to a person being treated for said mental condition a composition comprising, as active ingredient, the ethyl ester of benzoylecgonine or one of its pharmaceutically acceptable salts.

11. A method of claim 10, wherein said psychological pathologies are selected from the group consisting of schizophrenia, manic-depressive psychosis, paranoia and hallucinatory phenomena.

12. A composition of claim 4 wherein said salt is a salt of an inorganic or an organic acid selected from the group consisting of hydrochloride, hydrobromide, nitrate, sulphate, phosphate, formate, acetate, trifluoroacetate, fumarate, oxalate, tartrate, maleate, citrate, succinate, malate, methanesulphonate, benzenesulphonate, p-toluenesulphonate, and an amino acid.

13. A composition according to claim 1 wherein the pharmaceutically acceptable salt is a carboxylate cation resin or sulphonate cation resin.

14. The composition of claim 1 in the form of a chewing gum.

* * * * *